US010054533B2

(12) United States Patent
Naruse

(10) Patent No.: US 10,054,533 B2
(45) Date of Patent: Aug. 21, 2018

(54) METHOD FOR ESTIMATING PRESSURE LOSS OF AIR CLEANER AND DEVICE FOR ESTIMATING PRESSURE LOSS OF AIR CLEANER

(71) Applicant: KABUSHIKI KAISHA TOYOTA JIDOSHOKKI, Kariya-shi, Aichi-ken (JP)

(72) Inventor: Yuya Naruse, Aichi-ken (JP)

(73) Assignee: KABUSHIKI KAISHA TOYOTA JIDOSHOKKI, Kariya-shi, Aichi-ken (JP)

(*) Notice: Subject to any disclaimer, the term of this patent is extended or adjusted under 35 U.S.C. 154(b) by 59 days.

(21) Appl. No.: 15/057,287

(22) Filed: Mar. 1, 2016

(65) Prior Publication Data

US 2016/0258854 A1 Sep. 8, 2016

(30) Foreign Application Priority Data

Mar. 6, 2015 (JP) ................. 2015-044582

(51) Int. Cl.
*G01N 15/08* (2006.01)
*B01D 65/10* (2006.01)
(Continued)

(52) U.S. Cl.
CPC ........... *G01N 15/082* (2013.01); *B01D 65/10* (2013.01); *F02D 41/0007* (2013.01);
(Continued)

(58) Field of Classification Search
CPC ........... G01N 15/082; G01N 2015/084; B01D 65/10; B01D 46/0086; F02D 41/0007;
(Continued)

(56) References Cited

U.S. PATENT DOCUMENTS 6,343,473 B1 * 2/2002 Kanesaka ............... F02B 33/34
60/609
2006/0196182 A1 * 9/2006 Kimoto ................. F02B 33/44
60/605.1
(Continued)

FOREIGN PATENT DOCUMENTS

DE 102007044862 A1 * 4/2009 ............. F02M 35/09
JP 58-015895 Y2 3/1983
(Continued)

OTHER PUBLICATIONS

Translated DE 102007044862 A1.*
Communication dated Jul. 21, 2016, from the European Patent Office in counterpart European Application No. 16158263.0.

*Primary Examiner* — Natalie Huls
*Assistant Examiner* — Monica S Young
(74) *Attorney, Agent, or Firm* — Sughrue Mion, PLLC

(57) ABSTRACT

A method and a device for calculating a pressure loss of an air cleaner, wherein the air cleaner is disposed upstream of a compressor of a supercharger in an engine provided with a plurality of state quantity sensors, includes the step of calculating an outlet pressure of the compressor by using output values of the state quantity sensors, the step of calculating an inlet pressure of the compressor by using the outlet pressure and a characteristic map of the compressor, wherein the characteristic map shows a relationship between a ratio of the outlet pressure to the inlet pressure and a flow rate of gas flowing in an intake pipe of the engine, and the step of calculating the pressure loss of the air cleaner from the inlet pressure.

5 Claims, 4 Drawing Sheets

(51) Int. Cl.
  *F02M 35/10*   (2006.01)
  *F02D 41/18*   (2006.01)
  *F02M 35/09*   (2006.01)
  *F02D 41/00*   (2006.01)
  *B01D 46/00*   (2006.01)

(52) U.S. Cl.
  CPC ............. *F02D 41/18* (2013.01); *F02M 35/09* (2013.01); *F02M 35/10373* (2013.01); *B01D 46/0086* (2013.01); *F02D 2200/0406* (2013.01); *F02D 2200/0408* (2013.01); *G01N 2015/084* (2013.01); *Y02T 10/144* (2013.01)

(58) Field of Classification Search
  CPC ............. F02D 41/18; F02D 2200/0406; F02D 2200/0408; F02M 35/09; F02M 35/10373
  USPC ............................................................ 73/83
  See application file for complete search history.

(56) References Cited

U.S. PATENT DOCUMENTS

| | | | |
|---|---|---|---|
| 2006/0207252 A1* | 9/2006 | Isobe | F02D 23/02 60/601 |
| 2008/0022679 A1* | 1/2008 | Hara | F02B 37/18 60/602 |
| 2009/0055072 A1* | 2/2009 | He | F02D 41/0007 701/102 |
| 2010/0151294 A1* | 6/2010 | Rainville | H01M 8/04201 429/444 |
| 2011/0197580 A1* | 8/2011 | Andrasko | F02D 23/00 60/602 |
| 2013/0036804 A1 | 2/2013 | Uehara | |

FOREIGN PATENT DOCUMENTS

| | | |
|---|---|---|
| JP | 2000-097011 A | 4/2000 |
| JP | 2013-036382 A | 2/2013 |

* cited by examiner

METHOD FOR ESTIMATING PRESSURE LOSS OF AIR CLEANER AND DEVICE FOR ESTIMATING PRESSURE LOSS OF AIR CLEANER

BACKGROUND OF THE INVENTION

The present invention relates to a method for estimating pressure loss of an air cleaner that is disposed upstream of a compressor of a supercharger and a device for estimating pressure loss of an air cleaner.

Japanese Utility Model Publication No. S58-15895 and Japanese Patent Application Publications 2000-97011 and 2013-36382 disclose such a method and a device for estimating such pressure loss.

According to the method and the device disclosed in Japanese Utility Model Publication No. S58-15895, loading of the air cleaner element is calculated based on the negative pressures that are electrically detected by a pressure converter at the inlet and the outlet of an air cleaner element.

In the method and the device disclosed in Japanese Patent Application Publication no. 2000-97011 an air cleaner outlet pressure sensor is mounted in an intake pipe that is provided between an air cleaner and an airflow meter, and the pressure loss of the air cleaner is calculated based on the outlet pressure of the air cleaner detected by the pressure sensor and the flow of intake air detected by the airflow meter.

In the method and the device disclosed in Japanese Patent Application Publication no. 2013-36382, an intake pressure sensor is disposed in an intake passage between the airflow sensor and an engine, and the serviceable life parameter of the air cleaner is calculated based on the intake pressure detected by the pressure sensor and the flow of intake air detected by the airflow sensor.

However, the method and the device for estimating the pressure loss disclosed in the first and second Publications need additional sensors that are not usually mounted to the engine, namely a pressure converter in the first mentioned Publication and an air cleaner outlet pressure sensor in the second mentioned Publication, respectively for calculating (estimating) the pressure loss of the air cleaner. The number of parts is increased, and the production cost is increased, accordingly. The third method and device for estimating the pressure loss is applicable only to a naturally aspirated engine and inapplicable to an engine having a supercharger that includes a compressor disposed in the intake passage between the air cleaner and the engine.

The present invention, which has been made in light of the above described problems, is directed to providing a method that can estimate pressure loss of an air cleaner that is disposed in an intake passage of an engine having a supercharger without increasing the number of parts.

SUMMARY OF THE INVENTION

In accordance with an aspect of the present invention, there is provided a method for calculating a pressure loss of an air cleaner wherein the air cleaner is disposed upstream of a compressor of a supercharger in an engine provided with a plurality of state quantity sensors including the step of calculating an outlet pressure of the compressor by using output values of the state quantity sensors, the step of calculating an inlet pressure of the compressor by using the outlet pressure and a characteristic map of the compressor, wherein the characteristic map shows a relationship between a ratio of the outlet pressure to the inlet pressure and a flow rate of gas flowing in an intake pipe of the engine, and the step of calculating the pressure loss of the air cleaner from the inlet pressure.

Other aspects and advantages of the invention will become apparent from the following description, taken in conjunction with the accompanying drawings, illustrating by way of example the principles of the invention.

BRIEF DESCRIPTION OF THE DRAWINGS

The invention together with objects and advantages thereof, may best be understood by reference to the following description of the presently preferred embodiments together with the accompanying drawings in which.

DETAILED DESCRIPTION OF THE EMBODIMENTS

The following will describe an embodiment of the present invention with reference to the accompanying drawings and charts.

Figure 1:
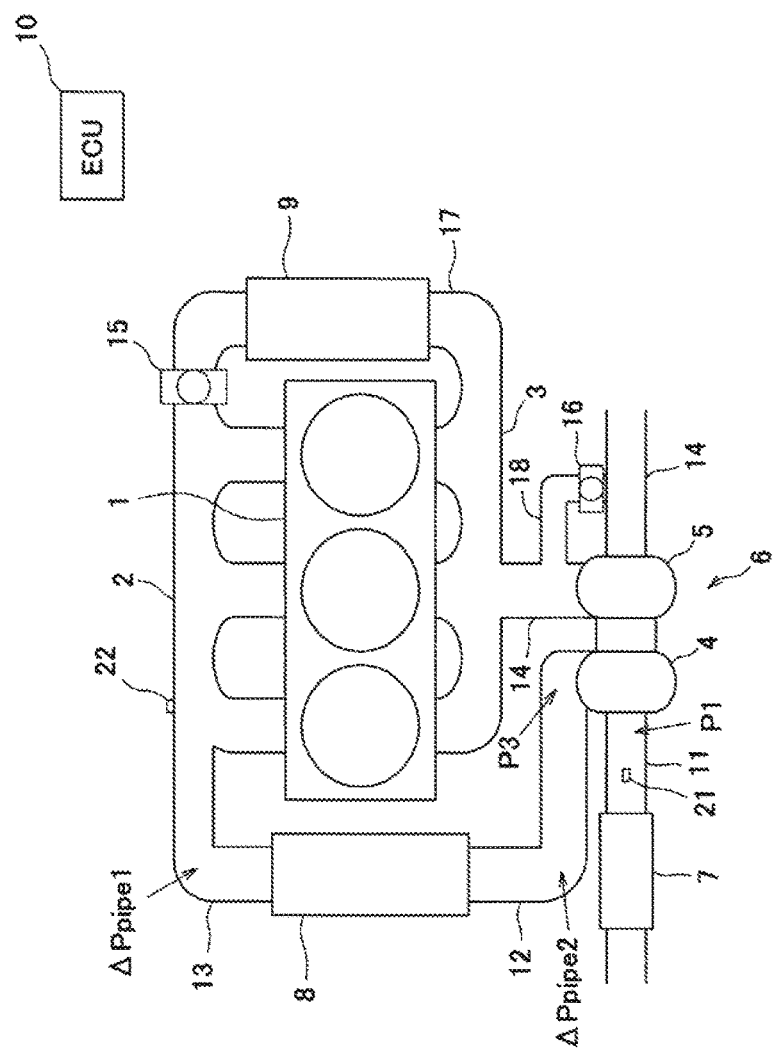
FIG. 1 is a schematic view showing an engine having a supercharger to describe a method for estimating pressure loss of an air cleaner according to an embodiment of the present invention.

Referring to FIG. 1, there is shown an engine 1 having a supercharger 6. The engine 1 is connected to an intake manifold 2 and an exhaust manifold 3. The intake manifold 2 is connected to an intake pipe 13 that is connected to an intercooler 8. The intercooler 8 is connected to an intake pipe 12, which is connected to an intake pipe 11 via a compressor 4 of the supercharger 6. The supercharger 6 is connected to an air cleaner 7. The flow of intake air of the engine 1 is measured by an airflow meter 21 (gas flow sensor) that is disposed in the intake pipe 11.

The exhaust manifold 3 is connected to an exhaust pipe 14 in which an exhaust turbine 5 of the supercharger 6 is disposed. The intake manifold 2 and the exhaust manifold 3 are connected by an EGR (exhaust gas recirculation) pipe 17, and an EGR cooler 9 is arranged in the EGR pipe 17. An EGR valve 15 is disposed between the intake manifold 2 and the EGR pipe 17 and regulates the flow of the exhaust gas that is to be recirculated back to the engine 1. The exhaust pipe 14 includes a bypass pipe 18 in which a wastegate valve 16 is provided. The wastegate valve 16 releases exhaust gas so as to control a supercharging pressure to the engine 1. Specifically, the wastegate valve 16 controls the flow of exhaust gas flowing through the bypass pipe 18. The supercharging pressure to the engine 1 is measured by a supercharging pressure sensor 22 that is mounted to the intake manifold 2.

Output signals from the airflow meter 21 and the supercharging pressure sensor 22 are sent to an ECU 10 (electric control unit or control device). The ECU 10 controls the EGR valve 15 and the wastegate valve 16.

The supercharger 6 that boosts the engine 1 is electrically driven and controls the rotation speed of the supercharger 6. A turbine wheel (not shown) of the exhaust turbine 5 and an impeller (not shown) of the compressor 4 are integrally formed via a turbine shaft (not shown). Exhaust gas from the engine 1 causes the turbine wheel to rotate, which drives to rotate the impeller. With the rotation of the impeller, the compressed air is supplied to the engine 1.

The rotation speed of the supercharger 6, or rotation speed of the turbo, is controlled by the ECU 10. The rotation speed of the supercharger 6 is measured by a rotation speed sensor (not shown) that is mounted to the supercharger 6 and an electric current sensor of an electric motor (not shown) that forms a part of the supercharger 6. The rotation speed sensor and the electric current sensor generate output signals to ECU 10 which convert such signals to signals indicative of rotation speed.

Figure 2:
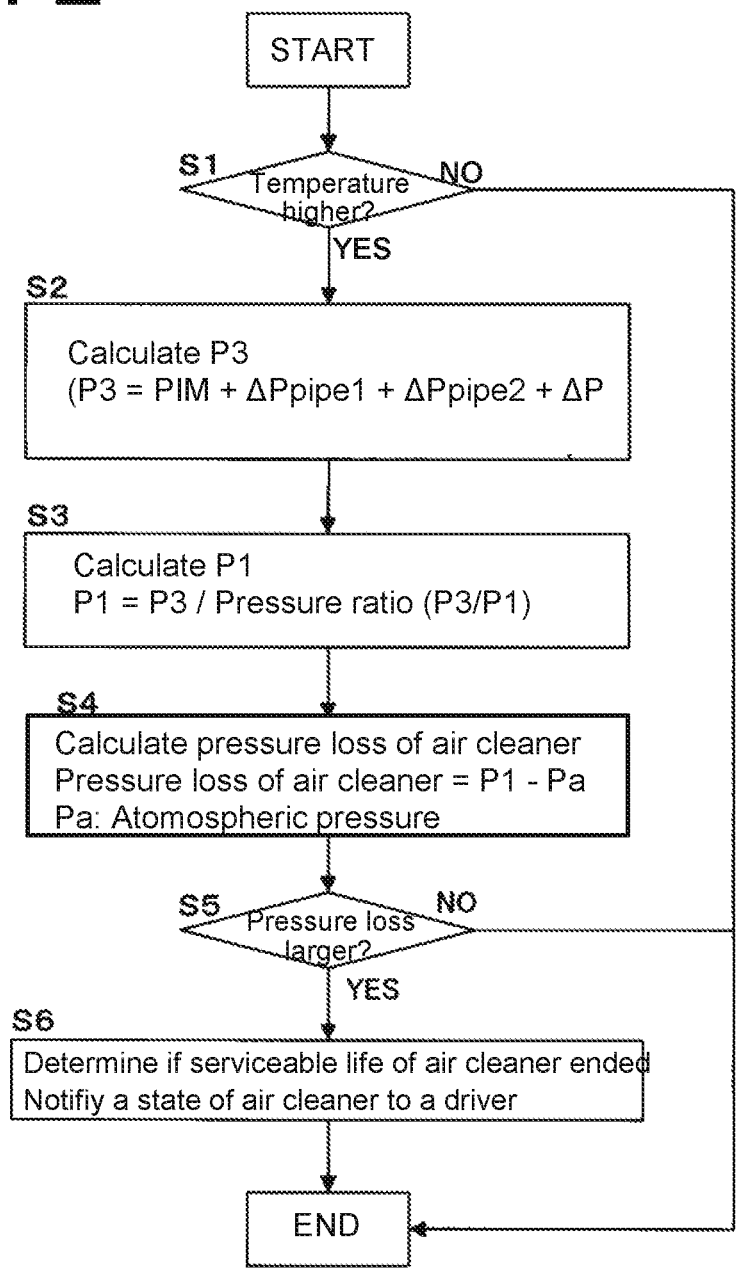
FIG. 2 is a flow chart of the method for estimating the pressure loss of the air cleaner.

The following will describe a method for estimating the pressure loss of the air cleaner 7 with reference to FIGS. 1 and 2. Each calculating steps shown in FIG. 2 is performed by ECU10.

Firstly, it is determined whether or not the temperature of cooling water of the engine 1 is higher than a specific temperature (step S1). If NO, or if the temperature is determined to be lower than the specific temperature, the program proceeds to END. Specifically, if the temperature of cooling water is low, there may exist ice in the intercooler 8 and accordingly there may occur a significant error in the estimation of the pressure loss in the intercooler 8 ($\Delta Pic$) based on the flow rate of the gas flowing through the intake pipes 11, 12, 13 that are measured by the airflow meter 21. Therefore, if the cooling water temperature is determined to be low in the step S1, the program proceeds to END.

If YES in the step S1, or if the cooling water temperature is determined to be higher than the specific temperature in the step S1, the outlet pressure P3 of the compressor 4 is calculated from the following equation (step S2, first operation).

$$P3 = PIM + \Delta Ppipe1 + \Delta Ppipe2 + \Delta Pic$$

wherein,
PIM: supercharging pressure to the engine 1
$\Delta Ppipe1$: pressure loss in the intake pipe 13
$\Delta Ppipe2$: pressure loss in the intake pipe 12
$\Delta Pic$: pressure loss in the intercooler 8

Figure 3:
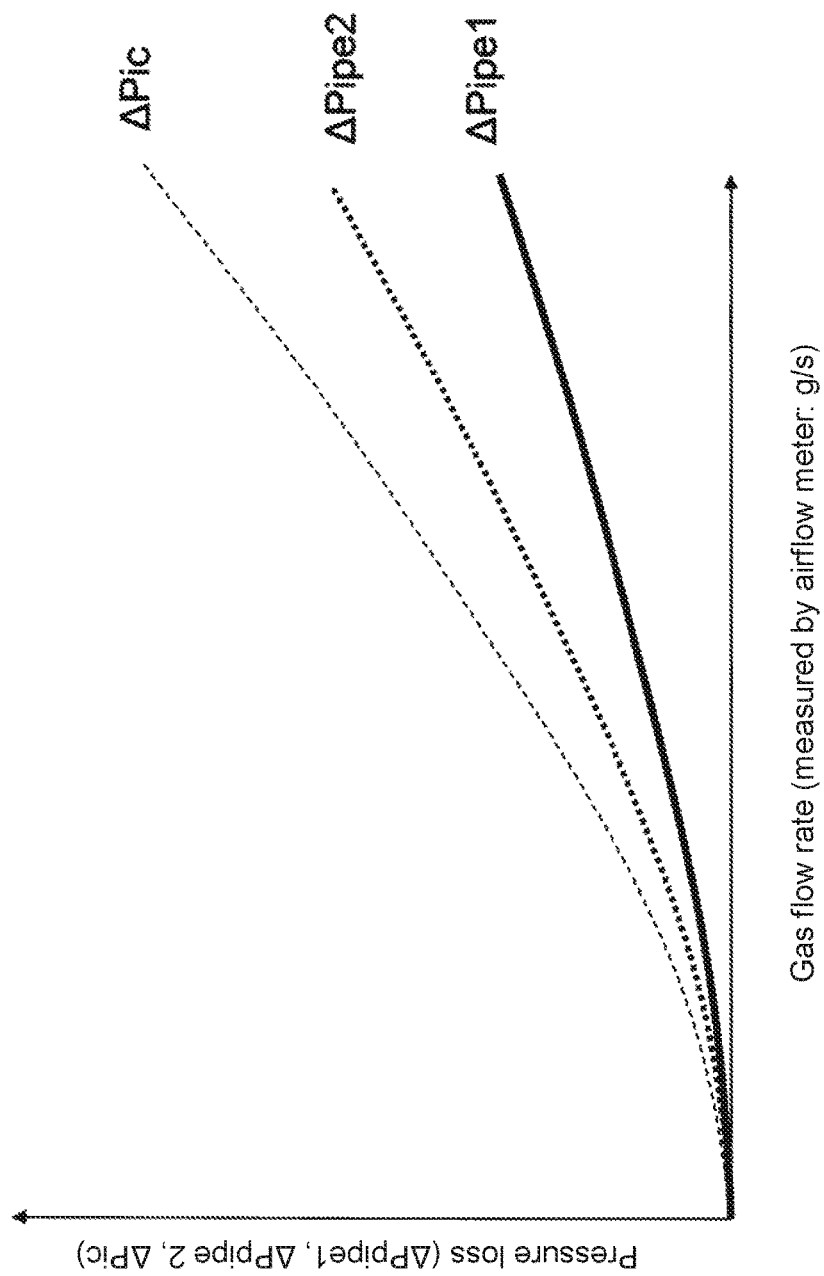
FIG. 3 is a chart showing a relationship between the gas flow and the pressure loss.

The supercharging pressure to the engine 1 (PIM) is detected by the supercharging pressure sensor 22. Referring to FIG. 3, there is shown a chart that has been made previously and illustrates the relationship between the gas flow and the pressure loss. The pressure loss in the intake pipe 13 ($\Delta Ppipe1$), the pressure loss in the intake pipe 12 ($\Delta Ppipe2$) and the pressure loss in the intercooler 8 ($\Delta Pic$) are calculated and determined based on the flow rate of gas (g/s) measured by the airflow meter 21 and the curves in the chart FIG. 3. The pressure losses in the intake pipes 12, 13 ($\Delta Ppipe1$, $\Delta Ppipe2$) and the pressure loss in the intercooler 8 ($\Delta Pic$) will not be increased by degradation over time.

Figure 4:
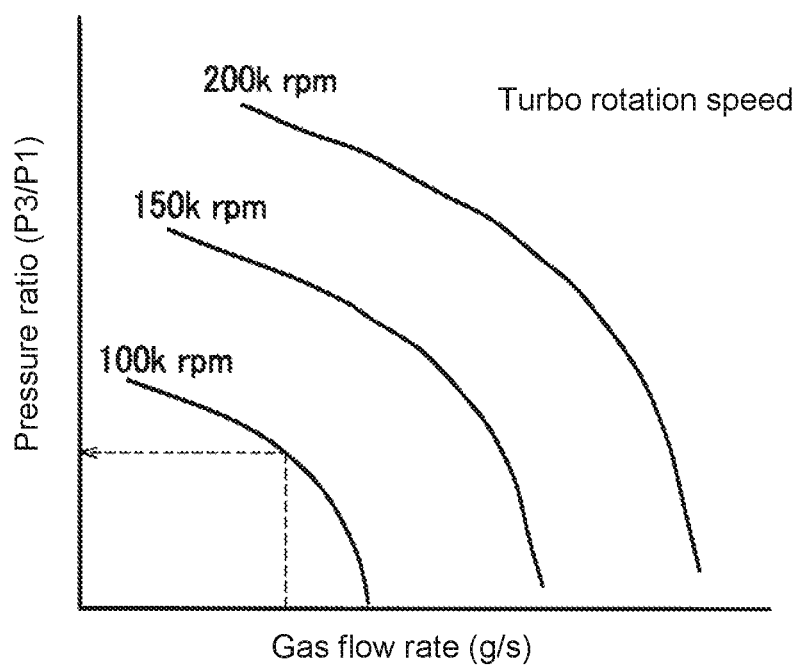
FIG. 4 is a map showing compressor characteristics.

Then, using the characteristics map of the compressor 4 in FIG. 4 showing the relationship between the pressure ratio P3/P1 (ratio of the outlet pressure P3 to the inlet pressure P1 of the compressor 4) and the flow rate of gas (g/s) flowing in the intake pipes 11, 12, 13 relative to the rotation speed of the turbo (or the rotation speed of the compressor 4). The inlet pressure P1 is calculated using the equation provided below (step S3, second operation).

$$P1 = P3/\text{Pressure ratio}(P3/P1)$$

After the inlet pressure P1 has been calculated, the pressure loss of the air cleaner 7 is calculated from the following equation (step S4, third operation). For the value of atmospheric pressure, 1013.25 hPa is set previously and stored in the ECU 10 in the present embodiment.

Pressure loss of air cleaner 7=P1−Atmospheric pressure.

Then, it is determined whether or not the pressure loss of the air cleaner 7 calculated at the steps S2 through S4 is larger than a predetermined value (step S5). If YES at the step S5, or if the pressure loss of the air cleaner 7 is determined to be larger than the predetermined value, the ECU determines based on the serviceable life data stored in the ECU that the serviceable life of the air cleaner 7 has ended and the element of the air cleaner 7 should be replaced with a new one, with simultaneous indication of such situation to a driver. If the pressure loss of the air cleaner 7 is significantly large, the air cleaner 7 may be in a temporarily abnormal state, for example, because of the ingress of any foreign objects such as snow and ice into the air cleaner 7. Such abnormal state of the air cleaner 7 should be notified to the driver by any signal on a display (step S6).

The above-described method for estimating pressure loss of the air cleaner 7 is performed by using the output values from the existing state quantity sensors that are used in a water cooled engine having an electric supercharger such as the airflow meter 21, the supercharging pressure sensor 22, the rotation speed sensor for the rotation speed controlled electric supercharger, the electric sensor, a temperature sensor that detects the temperature of the cooling water of the engine, with the result that the estimation of the pressure loss may be accomplished without increasing the number of parts for the device for performing the method.

The method for estimating the pressure loss of an air cleaner disclosed in Japanese Patent Application No. 2013-36382 is only applicable to a device having no EGR system. According to the present embodiment, on the other hand, the pressure loss of the air cleaner 7 is estimated by calculating the inlet pressure P1 of the compressor 4 based on the supercharging pressure to the engine 1 that is measured by the supercharging pressure sensor 22. Therefore, the method for estimating the pressure loss of the air cleaner of the present embodiment is applicable to an engine provided with an EGR system. In addition, the method of the present embodiment in which the inlet pressure P1 and the outlet pressure P3 of the compressor 4 are calculable needs no additional sensor for the supercharger 6.

Furthermore, according to the above-described method for estimating the pressure loss, the step S1 in which whether or not the temperature of the cooling water of the engine 1 is higher than a specific temperature is determined and, if YES in the step S1, or if the cooling water temperature is at the predetermined temperature or higher, the steps S2 through S4 for calculating the pressure loss of the air cleaner 7 are performed. This method effectively prevents miscalculation of the pressure loss due to the presence of ice in the intercooler 8 for an engine having a supercharger provided with an intercooler.

The above-described embodiment may be modified in various manners, as exemplified as below. The operation of the ECU 10 in the step S1 for determining whether or not the subsequent steps for estimating the pressure loss of the air cleaner 7 may be performed based on the atmospheric temperature instead of the temperature of the cooling water. In this case, the steps S2 through S4 for calculation of the pressure loss are performed if the atmospheric temperature is higher than a specific atmospheric temperature level. It is noted that the atmospheric temperature may be measured by an existing temperature sensor that is one of a plurality of state quantity sensors mounted to the vehicle. In addition, if the vehicle has any atmospheric pressure sensor, the pressure measured by the atmospheric pressure sensor may be used as the basis for calculation of the pressure loss.

If no intercooler 8 is provided in the engine 1, the step S1 may be omitted.

If the intake pipe 11 has a significant length, the pressure loss in the intake pipe 11 needs to be taken into consideration. In this case, the pressure loss of the air cleaner 7 may be calculated in the step S4 according to the following equation.

Pressure loss of air cleaner 7=$P1+\Delta P$pipe3(Pressure loss in intake pipe 11)−Atmospheric pressure In the case in which a supercharger is not electrically driven, or in the case of an exhaust gas driven turbocharger that is usually provided with no sensor to detect the rotation speed of the turbo, a sensor to detects the rotation speed of the turbo to be added to the turbocharger. This sensor is only the additional part and existing sensors that are usually mounted to a vehicle may be used for the calculation. In other word, the minimum number of parts may be increased, as compared with the conventional method for estimating the pressure loss of the air cleaner.

The scope of the present invention intends to include equivalents and all changes and modification that fall within the scope of the present invention.

What is claimed is:

1. A method for estimating pressure loss of an air cleaner, wherein the air cleaner is disposed upstream of a compressor of a supercharger in an engine comprising an intake manifold connected to the compressor through an intake pipe, and an intercooler disposed within the intake pipe, the engine being provided with a pressure sensor located on the intake manifold and an airflow meter, the method comprising:

the step of calculating an outlet pressure of the compressor by using output values of the pressure sensor and intake pressure loss in a first portion of the intake pipe downstream of the intercooler, the intercooler, and a second portion of the intake pipe upstream of the intercooler, between the pressure sensor and a point where the outlet pressure is calculated, wherein the intake pressure loss is determined by a chart showing a relationship between a flow rate of gas flowing through the intake pipe and the intercooler, and pressure loss in the first portion of the intake pipe, the intercooler, and the second portion of the intake pipe, the flow rate of gas being detected by the airflow meter;

the step of calculating an inlet pressure of the compressor downstream of the air cleaner by dividing the outlet pressure with a ratio of the outlet pressure to the inlet pressure shown on a characteristic map of the compressor, wherein the characteristic map shows a relationship between the ratio of the outlet pressure to the inlet pressure and the flow rate of gas flowing in the intake pipe of the engine; and the step of calculating the pressure loss of the air cleaner by comparing the inlet pressure with an atmospheric pressure upstream of the air cleaner.

2. The method for estimating pressure loss of the air cleaner according to claim 1, further comprising the step of determining whether or not one of a cooling water temperature of the engine and an atmospheric temperature is higher than a predetermined temperature, wherein the pressure loss of the air cleaner is calculated by performing the calculating steps if the cooling water temperature of the engine or the atmospheric temperature is higher than the predetermined temperature.

3. The method for estimating pressure loss of the air cleaner according to claim 1, wherein the airflow meter is a gas flow sensor that is mounted to a third portion of the intake pipe upstream of the compressor, wherein the ratio of the outlet pressure to the inlet pressure is calculated from the flow rate of gas relative to a rotation speed of the supercharger by using the characteristic map of the compressor.

4. A device for estimating pressure loss of an air cleaner, wherein the air cleaner is disposed upstream of an inlet disposed upstream of a compressor of a supercharger in an engine comprising an intake manifold connected to the compressor through an intake pipe, and an intercooler disposed within the intake pipe, the engine being provided with a pressure sensor located on the intake manifold, and an airflow meter being located in a third portion of the intake pipe upstream of the compressor, the device comprising:

a control unit programmed to:

calculate an outlet pressure of the compressor from output values of the pressure sensor and intake pressure loss in a first portion of the intake pipe downstream of the intercooler, the intercooler, and a second portion of the intake pipe upstream of the intercooler, between the pressure sensor and a point where the outlet pressure is calculated, wherein the intake pressure loss is determined by a chart showing a relationship between a flow rate of gas flowing through the intake pipe and the intercooler, and pressure loss in the first portion of the intake pipe, the intercooler, and the second portion of the intake pipe, the flow rate of gas being detected by the airflow meter;

calculate an inlet pressure of the compressor downstream of the air cleaner by dividing the outlet pressure with a ratio of the outlet pressure to the inlet pressure shown on a characteristic map of the compressor, wherein the characteristic map shows a relationship between the ratio of the outlet pressure to the inlet pressure and the flow rate of gas flowing in the intake pipe of the engine; and calculate the pressure loss of the air cleaner by comparing the inlet pressure with an atmospheric pressure upstream of the air cleaner.

5. The device for estimating pressure loss of the air cleaner according to claim 4, wherein the control unit further determines whether or not one of a cooling water temperature of the engine and an atmospheric temperature is higher than a predetermined temperature, and wherein the control unit calculates the pressure loss of the air cleaner if the cooling water temperature of the engine or the atmospheric temperature is higher than the predetermined temperature.

* * * * *